(12) United States Patent
Neu et al.

(10) Patent No.: US 6,699,501 B1
(45) Date of Patent: Mar. 2, 2004

(54) POLYELECTROLYTE COVERINGS ON BIOLOGICAL TEMPLATES

(75) Inventors: Björn Neu, Pasadena, CA (US); Hans Bäumler, Berlin (DE); Edwin Donath, Giesenhorst (DE); Sergio Moya, Berlin (DE); Gleb Sukhobukov, Moscow District (RU); Helmuth Möhwald, Bingen (DE); Frank Caruso, Golm (DE)

(73) Assignee: Max-Planck-Gesellschaft zur Forderung der Wissenschaften. e.V., Munich (DE)

( * ) Notice: Subject to any disclaimer, the term of this patent is extended or adjusted under 35 U.S.C. 154(b) by 0 days.

(21) Appl. No.: 09/743,367

(22) PCT Filed: Jul. 15, 1999

(86) PCT No.: PCT/EP99/05063

§ 371 (c)(1),
(2), (4) Date: Mar. 7, 2001

(87) PCT Pub. No.: WO00/03797

PCT Pub. Date: Jan. 27, 2000

(30) Foreign Application Priority Data

| Jul. 15, 1998 | (EP) | ............................................. 98113181 |
| Feb. 22, 1999 | (DE) | ........................................ 199 07 552 |

(51) Int. Cl.[7] ............................ A61K 9/14; A61K 9/16; A61K 9/50; A61K 9/51; A61K 9/54

(52) U.S. Cl. ...................... 424/463; 424/450; 424/460; 424/461; 424/462; 424/489; 424/490; 424/494; 424/496; 424/497; 424/498

(58) Field of Search ................................ 424/451, 489, 424/490, 463, 450, 455, 460, 461, 462, 494, 496, 497

(56) References Cited

FOREIGN PATENT DOCUMENTS

| WO | 95 26714 | 10/1995 |
| WO | 96 18498 | 6/1996 |
| WO | 96 30409 | 10/1996 |
| WO | 98 14180 | 4/1998 |

*Primary Examiner*—James M. Spear
(74) *Attorney, Agent, or Firm*—Fulbright & Jaworski L.L.P.

(57) ABSTRACT

The invention relates to a method for producing capsules provided with a polyelectrolyte covering, and to the capsules obtained using this method.

46 Claims, 10 Drawing Sheets

POLYELECTROLYTE COVERINGS ON BIOLOGICAL TEMPLATES

This application is a 371 of PCT/EP99/05063 filed Jul. 15, 1999.

The invention relates to a process for producing capsules with a polyelectrolyte shell, and to the capsules obtainable by the process.

Microcapsules are known in various embodiments and are used in particular for controlled release and targeted transport of active pharmaceutical ingredients, and for protecting sensitive active ingredients such as, for example, enzymes and proteins.

Microcapsules can be produced by mechanical/physical processes, or spraying and subsequent coating, chemical processes such as, for example, interfacial polymerization or condensation or polymer phase separation or by encapsulating active ingredients in liposomes. However, processes disclosed to date have a number of disadvantages.

German patent application 198 12 083.4 describes a process for producing microcapsules with a diameter of <10 μm, where several consecutive layers of oppositely charged polyelectrolyte molecules are applied to an aqueous dispersion of template particles. The template particles described in this connection are, in particular, partially crosslinked melamine-formaldehyde particles. After formation of the polyelectrolyte shell it is possible to disintegrate the melamine-formaldehyde particles by adjusting an acidic pH or by sulfonation.

It has been found, surprisingly, that polyelectrolyte capsules can also be formed with use of templates selected from biological cells, aggregates of biological or/and amphiphilic materials such as, for example, erythrocytes, bacterial cells or lipid vesicles. The encapsulated template particles can be removed by subsequent solubilization or disintegration.

The invention thus relates to a process for producing capsules with a polyelectrolyte shell, where several consecutive layers of oppositely charged polyelectrolyte molecules are applied to a template selected from aggregates of biological or/and amphiphilic materials, and the template is subsequently disintegrated where appropriate.

Examples of template materials which can be used are cells, for example eukaryotic cells, such as, for example, mammalian erythrocytes or plant cells, single-cell organisms such as, for example, yeasts, bacterial cells such as, for example, *E.coli* cells, cell aggregates, subcellular particles such as, for example, cell organelles, pollen, membrane preparations or cell nuclei, virus particles and aggregates of biomolecules, for example protein aggregates such as, for example, immune complexes, condensed nucleic acids, ligand-receptor complexes etc. The process of the invention is also suitable for encapsulating living biological cells and organisms. Likewise suitable as templates are aggregates of amphophilic materials, in particular membrane structures such as, for example, vesicles, for example liposomes or micelles, and other lipid aggregates.

Several oppositely charged polyelectrolyte layers are deposited on these templates. This is done by firstly dispersing the template particles preferably in a suitable solvent, for example an aqueous medium. It is then possible—especially when the template particles are cells or other biological aggregates—to add a fixing reagent in sufficient concentration to bring about at least partial fixation of the template particles. Examples of fixing reagents are aldehydes such as formaldehyde or glutaraldehyde, which are preferably added to the medium to a final concentration between 0.1–5% (w/w).

Polyelectrolytes mean in general polymers with groups which are capable of ionic dissociation and may be a constituent or substituent of the polymer chain. The number of these groups capable of ionic dissociation in polyelectrolytes is normally so large that the polymers are water-soluble in the dissociated form (also called polyions). In this connection, the term poly-electrolytes also means ionomers in which the concentration of ionic groups is insufficient for water solubility but which have sufficient charges to enter into self-assembly. The shell preferably comprises "true" polyelectrolytes. Depending on the nature of the groups capable of dissociation, polyelectrolytes are divided into polyacids and polybases.

On dissociation of polyacids there is formation of polyanions, with elimination of protons, which can be both inorganic and organic polymers. Examples of polyacids are polyphosphoric acid, polyvinylsulfuric acid, polyvinylsulfonic acid, polyvinylphosphonic acid and polyacrylic acid. Examples of the corresponding salts, which are also referred to as polysalts, are polyphosphate, polysulfate, polysulfonate, polyphosphonate and polyacrylate.

Polybases contain groups able to take up protons, for example by reaction with acids to form salts. Examples of polybases with groups capable of dissociation located on the chains or laterally are polyallylamine, polyethyleneimine, polyvinylamine and polyvinylpyridine. Polybases form polycations by taking up protons.

Polyelectrolytes suitable according to the invention are both biopolymers such as, for example, alginic acid, gum arabic, nucleic acids, pectins, proteins and others, and chemically modified biopolymers such as, for example carboxymethylcellulose and ligninsulfonates, and synthetic polymers such as, for example, polymethacrylic acid, polyvinylsulfonic acid, polyvinyiphosphonic acid and polyethyleneimine.

It is possible to employ linear or branched polyelectrolytes. The use of branched polyelectrolytes leads to less compact polyelectrolyte multifilms with a higher degree of porosity of the walls. To increase the capsule stability it is possible to crosslink polyelectrolyte molecules within and/or between the individual layers, for example by crosslinking amino groups with aldehydes. A further possibility is to employ amphiphilic polyelectrolytes, for example amphiphilic block or random copolymers with partial polyelectrolyte characteristics to reduce the permeability to small polar molecules. Such amphiphilic copolymers consist of units differing in functionality, for example acidic or basic units on the one hand, and hydrophobic units on the other hand, such as styrenes, dienes or siloxanes etc., which can be arranged as blocks or randomly distributed over the polymer. It is possible by using copolymers which change their structure as a function of the external conditions to control the permeability or other properties of the capsule walls in a defined manner. Suitable examples thereof are copolymers with a poly-(N-isopropylacrylamide) content, for example poly-(N-isopropylacrylamide-acrylic acid), which change their water solubility as a function of the temperature, via the hydrogen bonding equilibrium, which is associated with swelling.

The release of entrapped active ingredients can be controlled via the dissolution of the capsule walls by using polyelectrolytes which are degradable under particular conditions, for example photo-, acid- or baselabile polyelectrolytes. A further possibility for particular possible applications is to use conducting polyelectrolytes or polyelectrolytes with optically active groups as capsule components.

There are in principle no restrictions on the polyelectrolytes or ionomers to be used as long as the molecules used have a sufficiently high charge or/and have the ability to enter into a linkage with the underlying layer via other interactions such as, for example, hydrogen bonding and/or hydrophobic interactions.

Suitable polyelectrolytes are thus both low molecular weight polyelectrolytes or polyions and macromolecular polyelectrolytes, for example also polyelectrolytes of biological origin.

For the application of the polyelectrolyte layers to the template there is preferably firstly production of a dispersion of the template particles in an aqueous solution. A polyelectrolyte species with the same or the opposite charge as the surface of the template particle is then added to this dispersion. After removal of any excess polyelectrolyte molecules present, the oppositely charged polyelectrolyte species used to build up the second layer is added. Subsequently there are further alternate applications of oppositely charged layers of polyelectrolyte molecules, it being possible to choose for each layer with the same charge identical or different polyelectrolyte species or mixtures of polyelectrolyte species. The number of layers can in principle be chosen as desired and is, for example, 2 to 40, in particular 4 to 20, polyelectrolyte layers.

After application of the required number of layers, the enveloped template particles can—if desired—be disintegrated. The disintegration can take place by adding lytic reagents. Lytic reagents suitable in this case are those able to disintegrate biological materials such as proteins or/and lipids. The lytic reagents preferably contain a deproteinizing agent, for example peroxo compounds such as, for example, $H_2O_2$ or/and hypochlorite compounds such as, for example, sodium or potassium hypochlorite. The disintegration of the template particles surprisingly takes place within a short incubation time, for example 1 min to 1 h at room temperature. The disintegration of the template particles is substantially complete because even on examination of the remaining shells under the electron microscope there are no longer any residues of the particles detectable. On incorporation of biological polyelectrolytes into the shell it is also possible to produce empty layers within the polyelectrolyte shell.

Capsules obtainable by the process of the invention can be produced with diameters in the range from 10 nm to 50 $\mu$m, preferably 50 nm to 10 $\mu$m, also in shapes differing from spherical, that is to say anisotropic. The wall thickness is determined by the number of polyelectrolyte layers and can be, for example, in the range from 2 to 100 nm, in particular in the range from 5 to 80 nm. The capsules are also distinguished by their monodispersity, that is to say on selection of suitable templates it is possible to obtain capsule compositions with a proportion of less than 10%, and particularly preferably less than 1%, of capsules whose difference from the average diameter is >50%.

The capsules are very stable toward chemical, biological, organic and thermal stresses. They can be frozen or freeze-dried and then taken up again in suitable solvents.

Since the capsules represent microimpressions of the templates contained in them, and retain their shape even after removal of the templates, it is possible to produce anisotropic particles which comprise microimpressions of biological structures such as cells, virus particles or biomolecule aggregates.

The permeability properties in the shell can be modified by forming or altering pores in at least one of the polyelectrolyte layers. Such pores may be formed automatically on use of appropriate polyelectrolytes. It is additionally possible to employ nanoparticles with anionic or/and cationic groups or/and surface-active substances such as, for example, surfactants or/and lipids for modifying the permeability and other properties. The permeability can additionally be modified by varying the conditions prevailing on deposition of the polyelectrolytes. Thus, for example, a high salt concentration in the surrounding medium results in a high permeability of the polyelectrolyte shell.

A particularly preferred modification of the permeability of polyelectrolyte shells can be achieved be depositing lipid layers or/and amphiphilic polyelectrolytes on the polyelectrolyte shell after disintegration of the template particles. It is possible in this way to reduce very greatly the permeability of the polyelectrolyte shells for small and polar molecules. Examples of lipids which can be deposited on the polyelectrolyte shells are lipids which have at least one ionic or ionizable group, for example phospholipids such as, for example, dipalmitoylphosphatidic acid or zwitterionic phospholipids such as, for example, dipalmitoylphosphatidylcholine or else fatty acids or corresponding long-chain alkylsulfonic acids. On use of zwitterionic lipids it is possible to deposit lipid multilayers on the polyelectrolyte shell. Further polyelectrolyte layers can subsequently be deposited on the lipid layers.

The capsules produced by the process can be used for entrapping active ingredients. These active ingredients may be both inorganic and organic substances. Examples of such active ingredients are catalysts, in particular enzymes, active pharmaceutical ingredients, polymers, dyes such as, for example, fluorescent compounds, sensor molecules, that is to say molecules which react detectably to a change in surrounding conditions (temperature, pH), crop protection agents and aroma substances.

The capsules can also be used as microreaction chambers for chemical reactions or as precipitation or crystallization templates. Because of the fact that the permeability of the capsule walls can be controlled so that, for example, they allow low molecular weight substances to pass through but substantially retain macromolecules, the high molecular weight products resulting from a chemical reaction, for example polymers resulting from a polymerization, can be retained in the interior in a simple way during the synthesis. The reaction product synthesized at the same time in the external medium can be removed subsequently or even during the reaction, for example by centrifugation or/and filtration.

The supply of the reaction substrate can be controlled during the reaction by the diffusion through the capsule walls. New ways of intervening in the progress of reactions emerge from this. Since the external medium can be replaced continuously for example by filtration or else suddenly for example by centrifugation, the polymerization reaction can be stopped as desired by removing the substrate, or the monomer can be replaced. It is thus possible to produce defined copolymers or multipolymers in a novel way. Since the progress of the reaction can be controlled by the monomer supply through the permeation, it is possible to produce in the capsules products with novel and different molecular weight distributions, for example highly monodisperse products. Polymers synthesized inside capsules can be detected, for example, spectroscopically by titration with fluorescent dyes and by confocal microscopy. The gain in mass, and thus the reaction kinetics, can be followed by single-particle light scattering.

On use of anisotropic capsules for packing active ingredients or as reaction chambers, for example for syntheses or precipitation processes, and, where appropriate, subsequent disintegration of the template shells, it is possible to produce particle compositions as dispersions with predetermined shapes and forms. The invention thus also relates to anisotropic particle compositions which are obtainable by encapsulating active ingredients in a polyelectrolyte shell, for example by synthesis or precipitation and subsequent removal of the template, for example by thermal or chemical treatment. These anisotropic particles preferably have the shape of the biostructures used as template.

A further possibility is to use the capsules for introducing organic liquids such as, for example, alcohols or hydrocarbons, for example hexanol, octanol, octane or decane, or for encapsulating gases. Such capsules filled with an organic, water-immiscible liquid can also be employed for chemical reactions, for example polymerization reactions. The monomer can thus be specifically concentrated in the interior of the capsules through its distribution equilibrium. It is possible where appropriate for the monomer solution to be encapsulated in the interior even before the start of the synthesis.

However, it is also possible to encapsulate active ingredients which are unable, because of their size, to penetrate the polyelectrolyte shell. For this purpose, the active ingredient to be entrapped is immobilized on the template particle or is encapsulated by the template particle, for example by phagocytosis or endocytosis in the case of living cells. After disintegration of the template particles, the active ingredient is released inside the polyelectrolyte shell. It is expedient to choose the conditions for disintegration of the template particle in this case so that no unwanted decomposition of the active ingredient takes place.

The capsules can be employed in numerous areas of application, for example sensor systems, surface analysis, as emulsion carriers, microreaction chambers such as, for example, for catalytic processes, polymerization, precipitation or crystallization processes, in pharmacy and medicine, for example for targeting of active ingredients or as ultrasonic contrast agents, in food technology, cosmetics, biotechnology, information technology and the printing industry (encapsulation of dyes). The capsules can further be employed for building up microcomposites or nanocomposites, that is to say materials consisting of at least two different materials and having a microscopic or nanoscopic arrangement.

Yet another aspect of the invention comprises partial disintegration of the template particles preferably in fixed form before the polyelectrolyte coating by treatment with a lytic reagent. Stopping the lytic process at the appropriate time results in partially disintegrated structures, for example toroidal structures with a hole in the middle, which can subsequently be coated. Subsequent complete degradation of the template particles results in annular capsules. This is an entirely novel type of topology with interesting possible applications, for example in optics (micro whispering gallery effect).

BRIEF DESCRIPTION OF THE DRAWINGS

The invention is explained further by the following examples and figures. These show.

EXAMPLES

1. Preparation of Polymer Shells with Bovine or Human Erythrocytes as Template The plasma is removed by centrifugation from fresh human or ox blood. This is followed by washing twice with an isotonic phosphate-buffered saline solution PBS (5.8 mM phosphate buffer pH 7.4, KCl 5.6 mM, NaCl 150 mM). The erythrocytes are then fixed with glutaraldehyde in a concentration of 2%. For this purpose, 1 ml of the erythrocyte sediment is made up with 1 ml of PBS. Then 8 ml of a glutaraldehyde solution (1 part of glutaraldehyde (25% strength aqueous solution) and 9 parts of PBS) are added dropwise to this solution. After acting for 60 min at 20° C., the solution is centrifuged and the erythrocytes are washed four times in double-distilled water. The fixed erythrocytes are then made up with unbuffered 154 mM NaCl solution.

The next step which follows is consecutive adsorption of two oppositely charged polyelectrolytes. Since the initial charge of the fixed erythrocytes is negative, it is preferred to use firstly positively charged poly(allylamine) hydrochloride (PAH) with a molecular weight between 50 and 60 kD (Aldrich). However, it is also possible to deposit a negatively charged polyelectrolyte as first layer on the erythrocytes. To coat the erythrocytes, 4 ml of solution with a concentration of 0.5 g/dl PAH and 0.5 M NaCl are made up for an erythrocyte concentration of about 2.5% (v/v). After acting for 10 min at 20° C., the erythrocytes are centrifuged and washed twice in a 154 mM NaCl solution. This is followed by adsorption of the second layer. For this purpose, negatively charged sodium poly(styrenesulfonate) (PSS) with a molecular weight of 70 kD is used. To apply the first PSS layer to the erythrocytes already coated with PAH, 4 ml of solution with a concentration of 0.5 g/dl PSS and 0.5 M NaCl and an erythrocyte concentration of about 2.5% (v/v) are made up. After acting for 10 min at 20° C., the erythrocyes are centrifuged and washed twice in a 154 mM NaCl solution. The application of PAH and PSS layers can be repeated as often as required. For example, it is possible to apply 5 PAH layers and 5 PSS layers.

To disintegrate the template, the fixed erythrocytes are pipetted into a 1.2% strength NaOCl solution. Also suitable are commercially available deproteinizers (product, manufacturer) or drain cleaners (for example Chlorix, manufacturer). They are allowed to act for about 20 min at 20° C., and monitoring is possible visually by the disappearance of the turbidity of the solution. The remaining polymer shells are then washed in an NaCl solution.

2. Preparation of Polymer Shells with E.coli Bacteria or Yeasts as Template

The E.coli cells are initially separated from the nutrient medium by washing twice in an isotonic PBS solution. They are then fixed using glutaraldehyde. For this purpose, the sediment of coli bacteria is made up to 2 ml with PBS. To this solution are added 8 ml of a glutaraldehyde solution to a final concentration of 2%. After acting for 60 min at 20° C., the solution is centrifuged and the fixed E.coli cells are washed four times in double-distilled water.

This is followed by consecutive adsorption of two oppositely charged polyelectrolytes as described in example 1.

Yeast cells were also coated—without previous fixation—in a corresponding manner.

3. Deposition of Lipid Layers on Polyelectrolyte Shells

Two different processes were used to deposit lipid layers on polyelectrolyte shells.

3.1

200 µl of a suspension of polyelectrolyte shells are resuspended in methanol by repeated washing. In place of pure methanol, after the third wash 500 µl of a lipid solution of, for example, 1 mg/ml dipalmitoylphosphatidic acid (DPPA) or dipalmitoylphosphatidylcholine (DPPC) in methanol are added to the sediment. The shells are resuspended in this methanolic lipid solution, and the suspension is kept at a temperature of 90° C. in a waterbath. The evaporating methanol is replaced by dropwise addition of water in 20 µl portions. Replacement of 700 µl of methanol by water takes about 30 min.

After completion of the evaporation, the suspension of shells is washed three times with water and repeatedly centrifuged. The lipid-coated shells can be sedimented by centrifugation at 25 000 rpm for 20 min.

3.2

Dispersions of DPPA or 90% DPPC and 10% DPPA with a concentration of 1 mg of lipid/ml in water are produced by ultrasonic treatment. 500 µl of the resulting dispersion of lipid vesicles are added to 200 µl of a concentrated suspension of shells. After 30 min, the samples are centrifuged at 25 000 rpm for 20 min. The supernatant is removed and replaced by water. This procedure is repeated three times. This results in a concentrated suspension of lipid-coated shells.

4. Entrapment of Organic Solvents in Polyelectrolyte Shells

An aqueous suspension of polyelectrolyte shells is centrifuged at 3000 rpm for 5 min. After removal of the supernatant, methanol is added. The shells are resuspended and centrifuged at 4000 rpm for 10 min. The supernatant is again removed, methanol is added and the sample is centrifuged under the same conditions as before. This procedure is repeated three times. After the last centrifugation with methanol, the supernatant is replaced by hexanol. The shells are resuspended and centrifuged at 5000 rpm for 10 min. This procedure is again repeated three times.

A similar procedure is used to entrap octanol, octane or decane in the shells, using as starting material the shells present in a hexanol solution. The centrifugation speed is increased to 7000 rpm (10 min) for octanol and octane and to 7500 rpm (10 min) for decane.

Finally, the resulting sediment is resuspended in water. The shells remain in the aqueous phase, while the solvent traces which are still present in the sediment form a second organic phase between the shells. It can be shown by using fluorescent markers for the organic and aqueous phases with the aid of confocal microscopy that the shells are filled with organic solvent.

The described procedure makes it possible to produce a very stable emulsion of nonpolar liquids in water. As a consequence of the monodispersity of the original shells, the produced emulsion is likewise monodisperse. Another advantage is that even the shape of the individual droplets can be controlled—depending on the template used. This makes it possible to produce emulsions with surface:volume ratios which differ from those of a sphere.

5. Characterization of Polyelectrolyte Shells

Figure 1A:
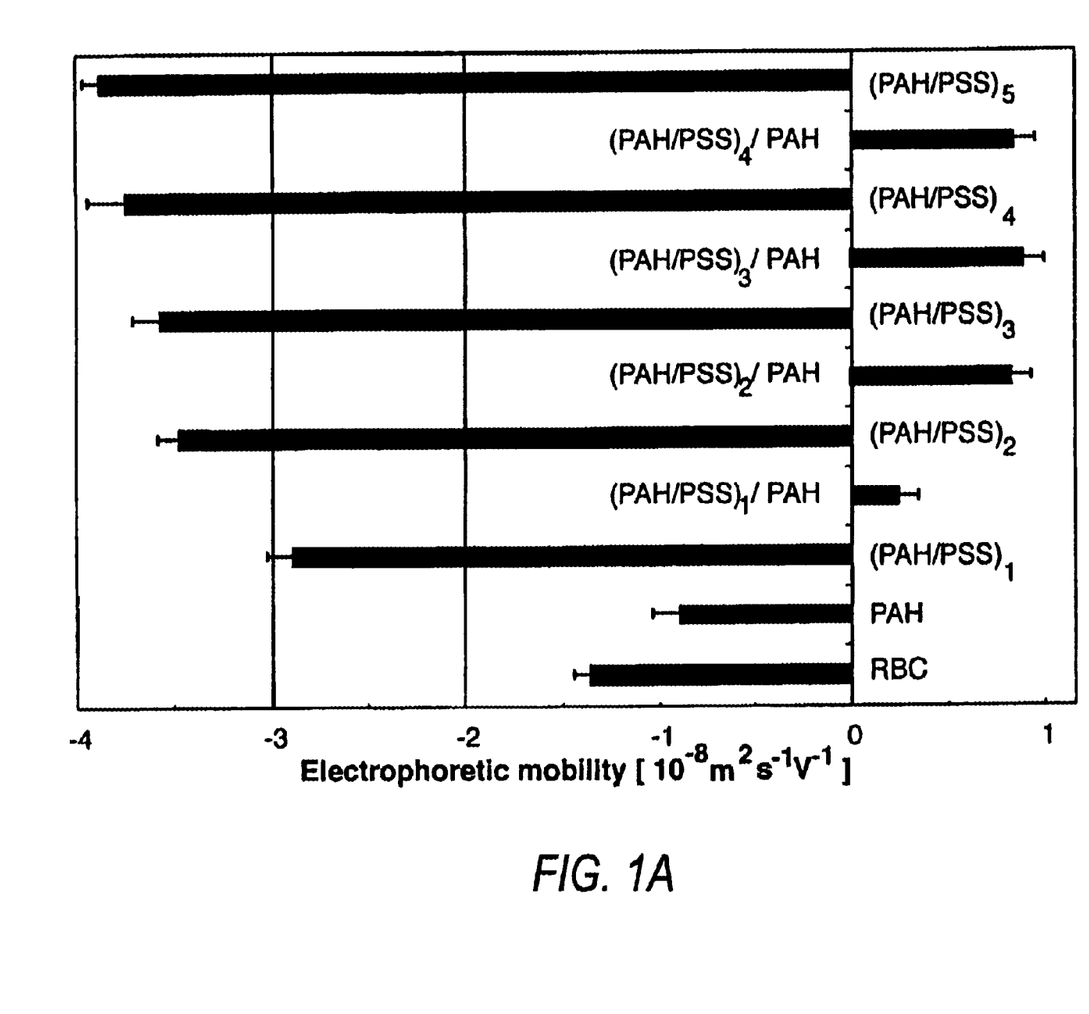
FIG. 1A and FIG. 1B the changes in the zeta potential (A) FIG. 1A and the increase in the fluorescence intensity (B) FIG. 1B as a function of the number of layers on deposition of poly(styrenesulfonate sodium salt) (PSS) and poly(allylamine hydrochloride) (PAH) on human erythrocytes fixed with glutaraldehyde.
Figure 1B:
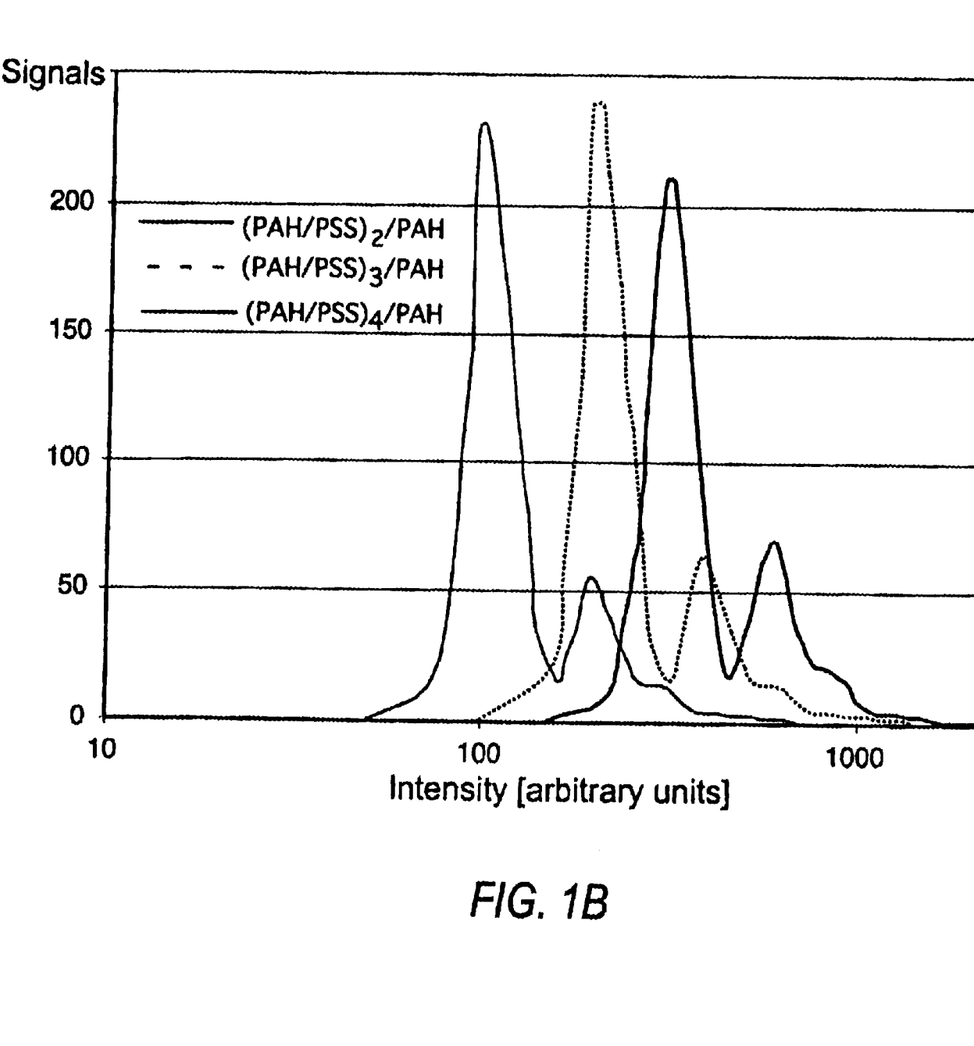

FIG. 1A and FIG. 1B shows the changes in the zeta potential (A) FIG. 1A and the increase in the fluorescence intensity (B) FIG. 1B as a function of the number of layers on deposition of poly(styrenesulfonate sodium salt) and poly(allylamine hydrochloride) on human erythrocytes pretreated with glutaraldehyde. The zeta potential is determined by electrophoretic mobility measurements (Elektrophor, Hasotec) in physiological saline solution. The fluorescence intensity distributions are recorded by flow cytometry (FACScan, Becton Dickinson) using FITC-labeled PAH in three consecutive layer-deposition cycles.

Figure 2:
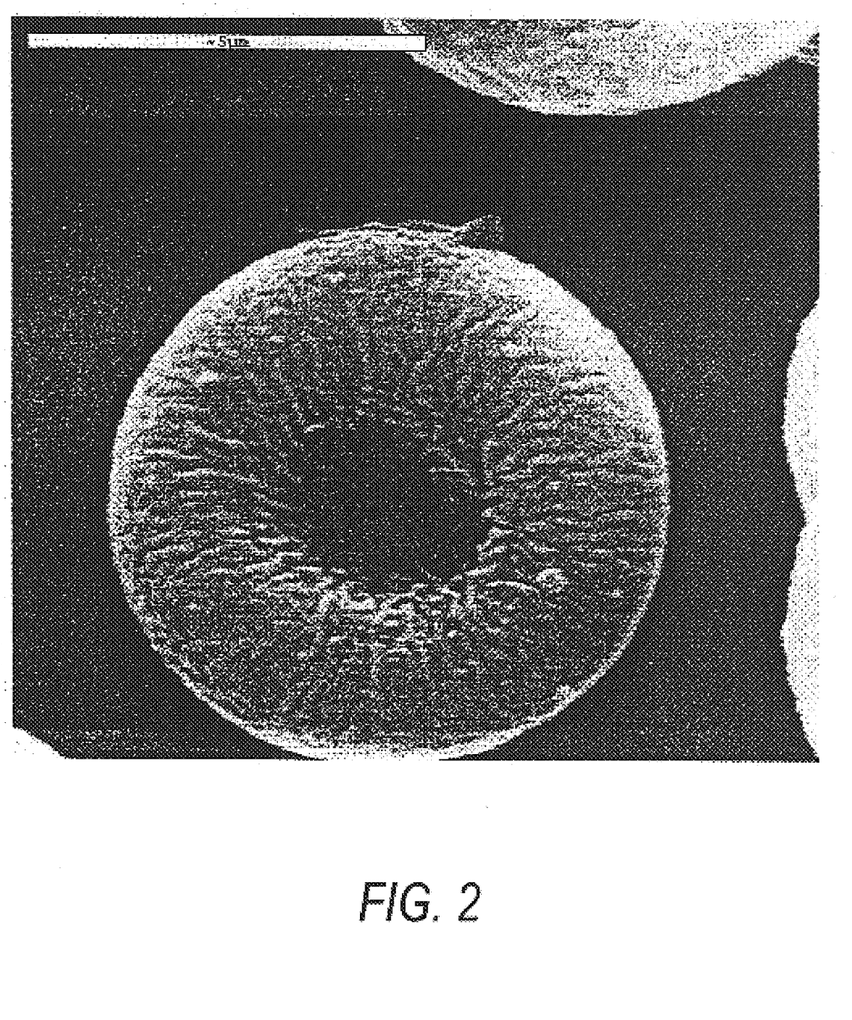
FIG. 2 a scanning electron micrograph of a discocyte covered with ten layers of PSS and PAH.

FIG. 2 shows the scanning electron micrograph of a discocyte covered with ten layers of PSS and PAH. The drying process leads to the development of longitudinal folds in the polyelectrolyte layer along the edge of the cell.

Figure 3A:
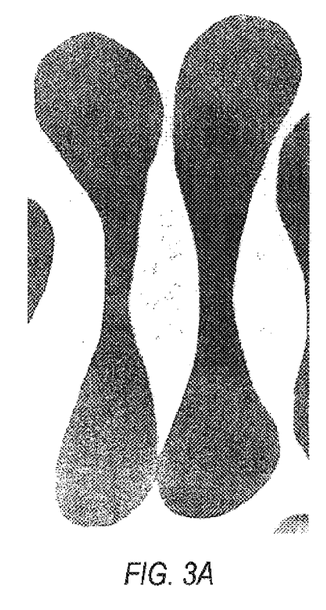
FIG. 3 transmission electron micrographs of an uncoated (A) and of a coated (B) discocyte, and of a polyelectrolyte shell (C) obtained after disintegration of the coated discocyte.
Figure 3B:
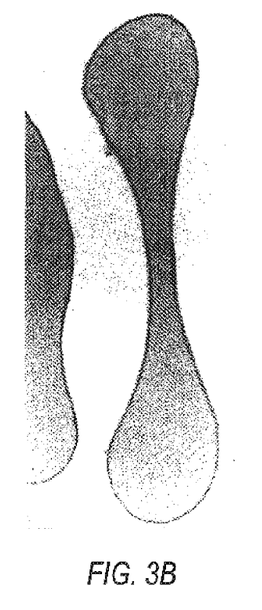
Figure 3C:
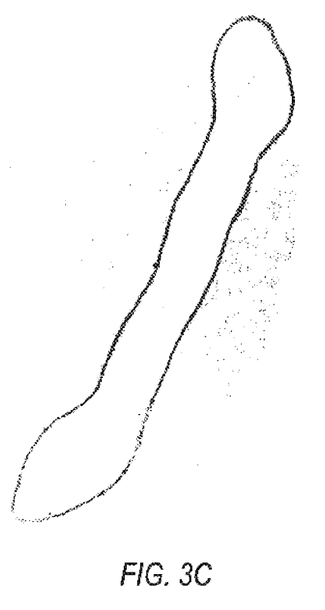

FIG. 3 shows transmission electron micrographs of uncoated (A) and coated (B) discocytes. The polyelectrolyte shell is clearly evident. The polyelectrolyte shell (C) obtained after solubilization of the cell shows two surprising properties. The magnifications are 1:15000 for A and B and 1:17000 for C. In the first place, it is similar to the shape of the original cell, and in the second place it appears to be completely empty without any fissures or major pores being evident in the shell.

Figure 4A:
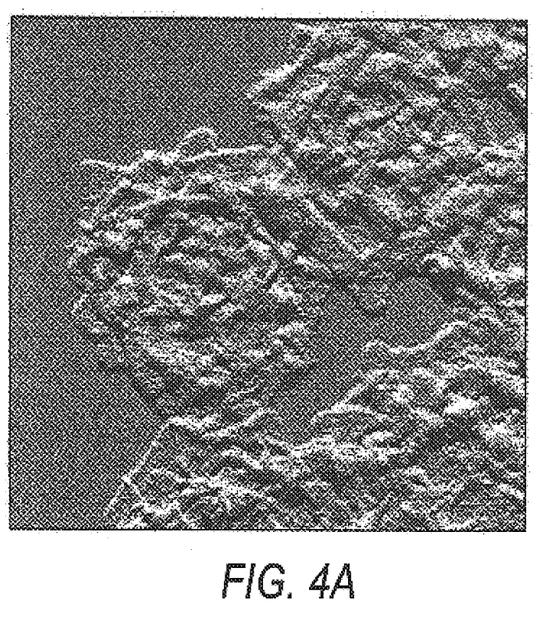
FIG. 4 atomic force micrographs of polyelectrolyte shells deposited on discocytes (A) and echinocytes (B).
Figure 4B:
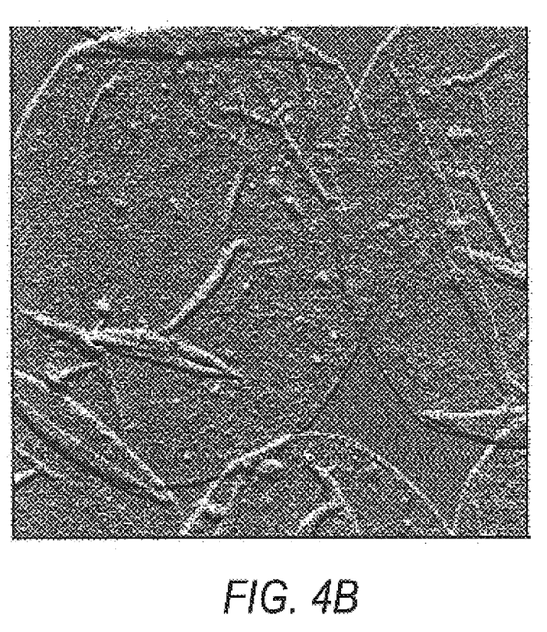
Figure 5A:
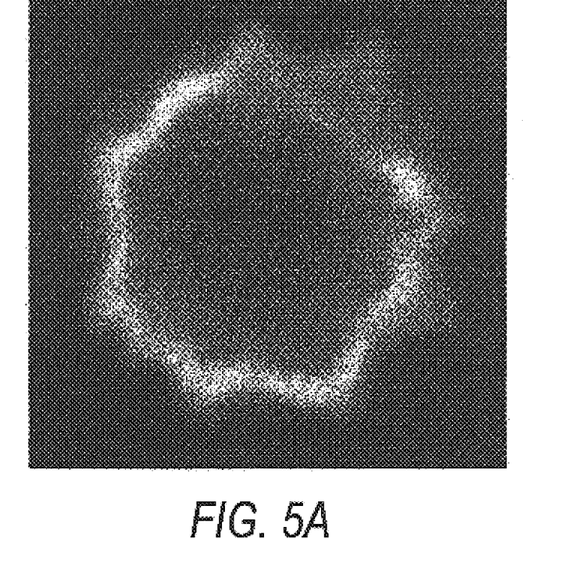
FIG. 5 images recorded with a confocal microscope of polyelectrolyte shells deposited on echinocytes and consisting of 11 PSS/PAH layers.
Figure 5B:
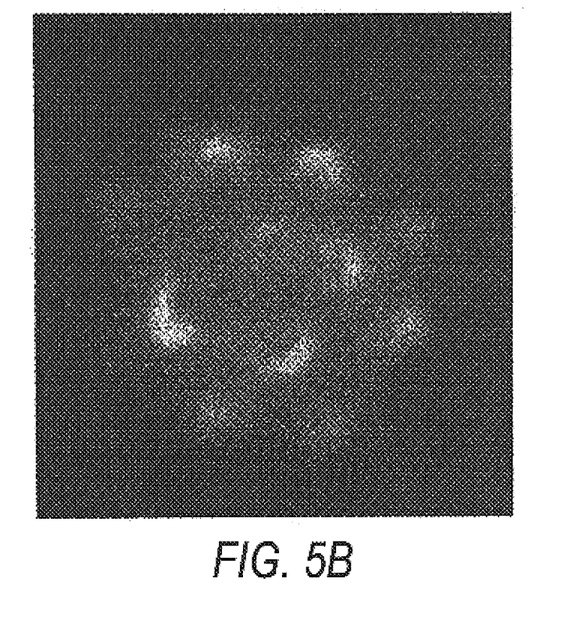

FIG. 4 depicts two images (width 10 µm) produced by atomic force microscopy (AFM) showing polyelectrolyte shells composed of a total of 9 layers deposited on a discocyte (A) and an echinocyte (B). Whereas the shells deposited on an ellipsoidal discocyte show only a few folds, the process of deposition on a star-like echinocyte results in well-structured shells on which even the projections of the original template are evident. This is made even clearer by the confocal micrographs of a polyelectrolyte shell composed of eleven PSS/PAH layers deposited on an echinocyte which are shown in FIG. 5. The outer layer consists of FITC-labeled PAH. The width of the images is 7 µm. The scans were made in 2 planes separated by a distance of 1 µm. Scan A runs through the upper part of the shell which has been applied to a glass support. It is evident from these images that the interior of the shell is empty, even in the region of the projections.

Figure 6A:
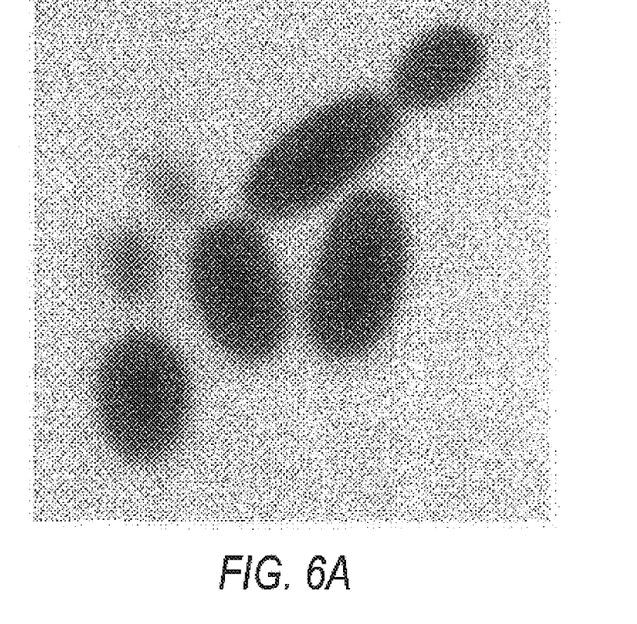
FIG. 6 images recorded with a confocal microscope of polyelectrolyte shells filled with 6-carboxyfluorescein.

FIG. 6 shows images recorded with a confocal microscope of polyelectrolyte shells consisting of 10 PSS/PAH layers deposited on discocytes. The shells were treated with a 100 µm 6-carboxyfluorescein (6-CF) solution. A fluorescence is evident inside the shells in FIG. 6A. This shows that the 6-CF molecules are able to penetrate inside the shell.

It was not possible to find any fluorescence on incubation of the shells with 100 nM 6-CF. This shows that treatment with the lytic reagent degrades or/and blocks the PAH amino groups capable of binding 6-CF. Because of the low concentration of 6-CF, the solution fluorescence is too low to be detectable as background.

Figure 6B:
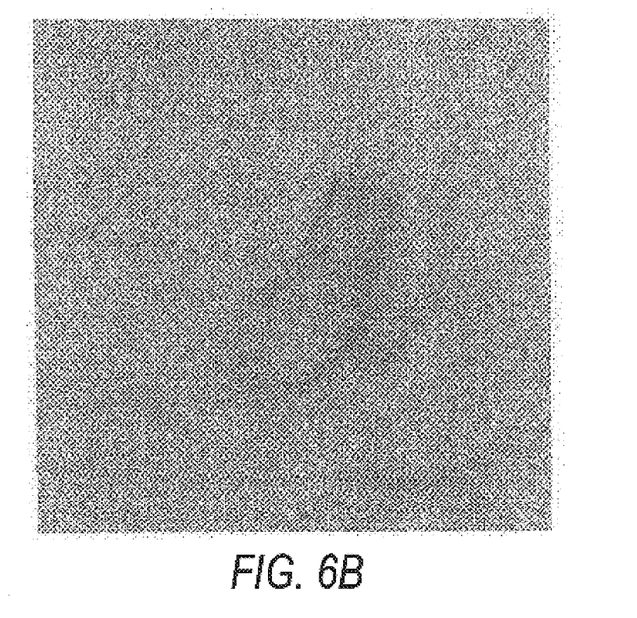

Adsorption of dipalmitoylphosphatidic acid (DPPA) or zwitterionic lipids, for example dipalmitoylphosphatidylcholine (DPPC), on polyelectrolyte shells as in example 3 by evaporation results in polyelectrolyte shells covered with stable lipid layers. The lipid layer substantially prevents penetration of 6-CF into the shell (FIG. 6 B). The width of the images depicted in FIGS. 6A and 6B is 16 and 15 μm respectively. Further experiments showed that the lipid layers are stable for at least 4 weeks and that further polyelectrolyte layers can be deposited on the lipid layers without damaging the underlying lipid layer.

The technique of electrorotation (Arnold et al., J. Phys. Chem. 91 (1987), 5093; Fuhr et al., In: Electromanipulation of Cells, U. Zimmermann and G. A. Neil, editors, CRC Press, Boca Raton (1996), 259–328; Pruger et al., Biophys. J. 72 (1997), 1414) is a spectroscopic method which makes it possible to investigate the dielectric properties of multilayer structures. This entails a rotating electrical field in the kHz to MHz range being applied to the suspension of particles. The induced dipole moment forms an angle with the applied field vector when the speed of rotation of the field is too fast for the induced dipole moment to be able to follow it. The result is that the particle acquires a torque which in turn leads to a detectable rotation of the particle itself. An electrorotation spectrum is obtained by measuring the speed of rotation of the particles as a function of the rotation frequency of the external electric field.

Figure 7:
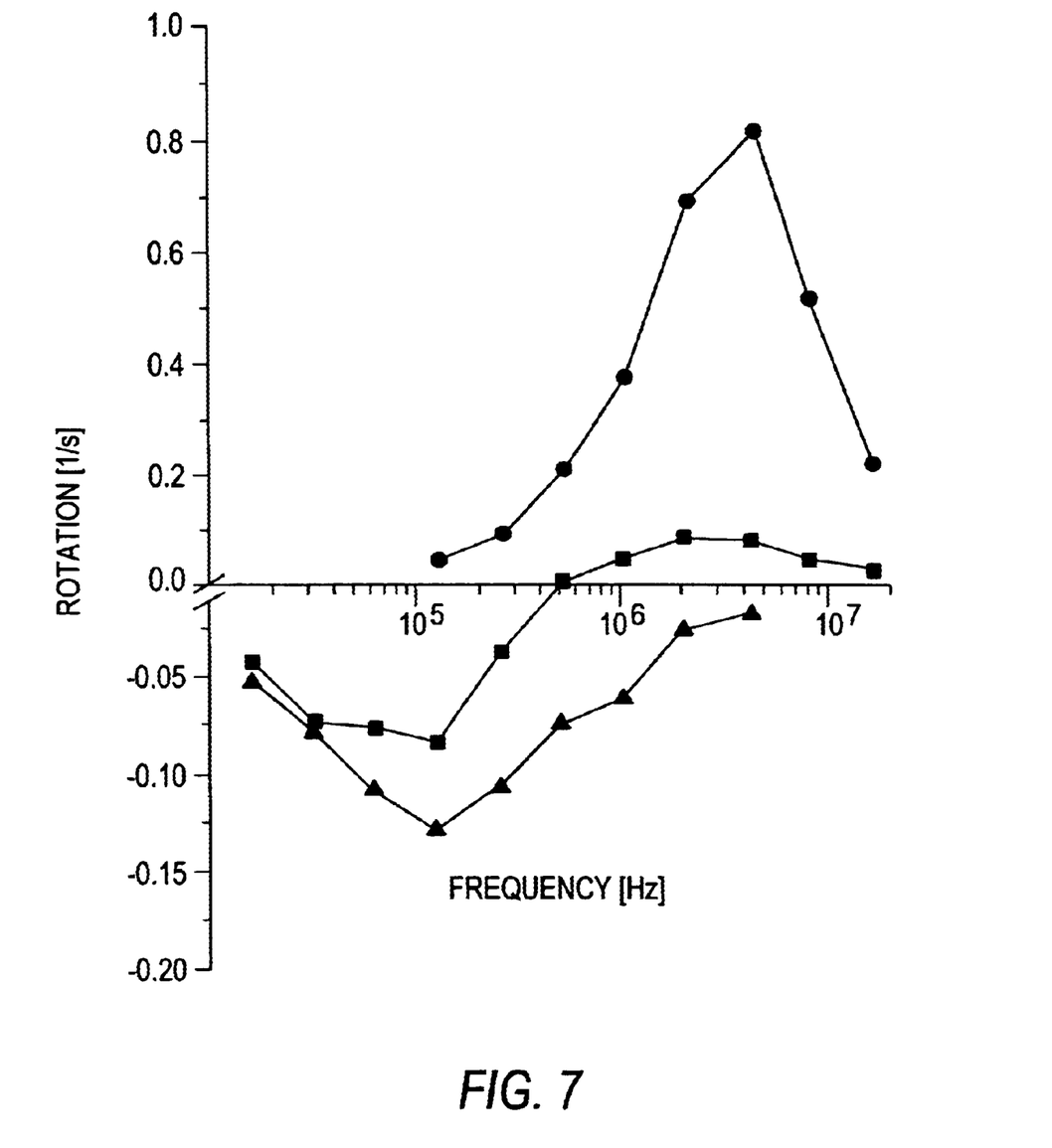
FIG. 7 electrorotation spectra of polyelectrolyte shells on discocytes without additional coating (A) or coated with DPPA (B) or DPPC (C).

FIG. 7 shows three typical electrorotation spectra for an uncoated polyelectrolyte shell as control (A), a DPPA-coated polyelectrolyte shell (B) and a DPPC-coated polyelectrolyte shell (C). The conductivity of the aqueous phase outside the shells was 2000 μS/cm, 80 μS/cm and 100 μS/cm, respectively. The presence of an insulating lipid layer leads to a negative direction of rotation in the kHz range. The highly conductive polyelectrolyte shell (about $10^4$ μS/cm) produces the positive peak detectable for the control in the MHz region. The poorly conductive DPPA layer is short-circuited at high frequencies. The absence of a positive rotation in the case of DPPC coating indicates the presence of lipid multilayers. These results show that polyelectrolyte multilayers can be successfully coated with lipids to control the permeability, and that the coated shells have low permeability for ionic compounds such as salts.

Figure 8A:
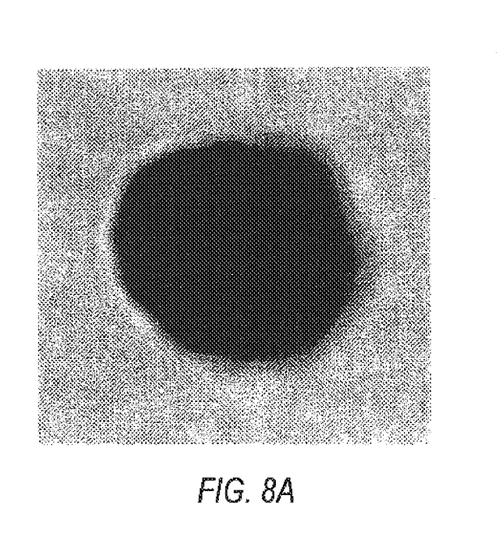
FIG. 8 the image of a polyelectrolyte shell deposited on a discocyte under a light microscope (A) and the corresponding scanning electron micrograph (B).
Figure 8B:
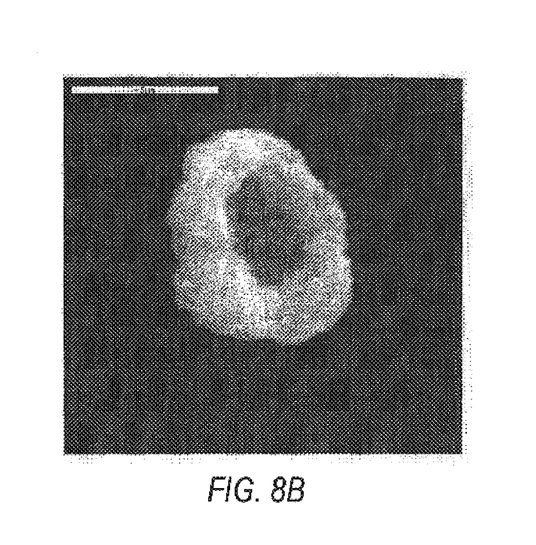

The empty polyelectrolyte shells can also be used for the controlled precipitation or crystallization of organic or inorganic materials. For this purpose, polyelectrolyte shells templated on discocytes are incubated in a 30 mM 6-CF solution at pH 7. The pH was then rapidly changed to a value of 3.5, at which 6-CF is substantially insoluble. After incubation for 1 to 12 h, a mixture of apparently completely 6-CF-filled and empty shells was obtained. FIG. 8A shows the light micrograph of a polyelectrolyte shell (10 layers) and FIG. 8B shows the corresponding scanning electron micrograph. The completely dark image A is attributable to the strong adsorption of the crystallized 6-CF. The SEM image shows that the 6-CF which has crystallized inside the shell assumes the shape of the original template. The width of image A is 8 μm. Further experiments showed that rhodamine B can be precipitated by increasing the pH. The precipitation of active ingredients can also be induced by other measures, for example solvent exchange, salt precipitation etc. These results show that the polyelectrolyte shells can be used as templates for crystallization or precipitation processes, making it possible to control the size and shape of colloidal particles produced by the reaction.

Figure 9:
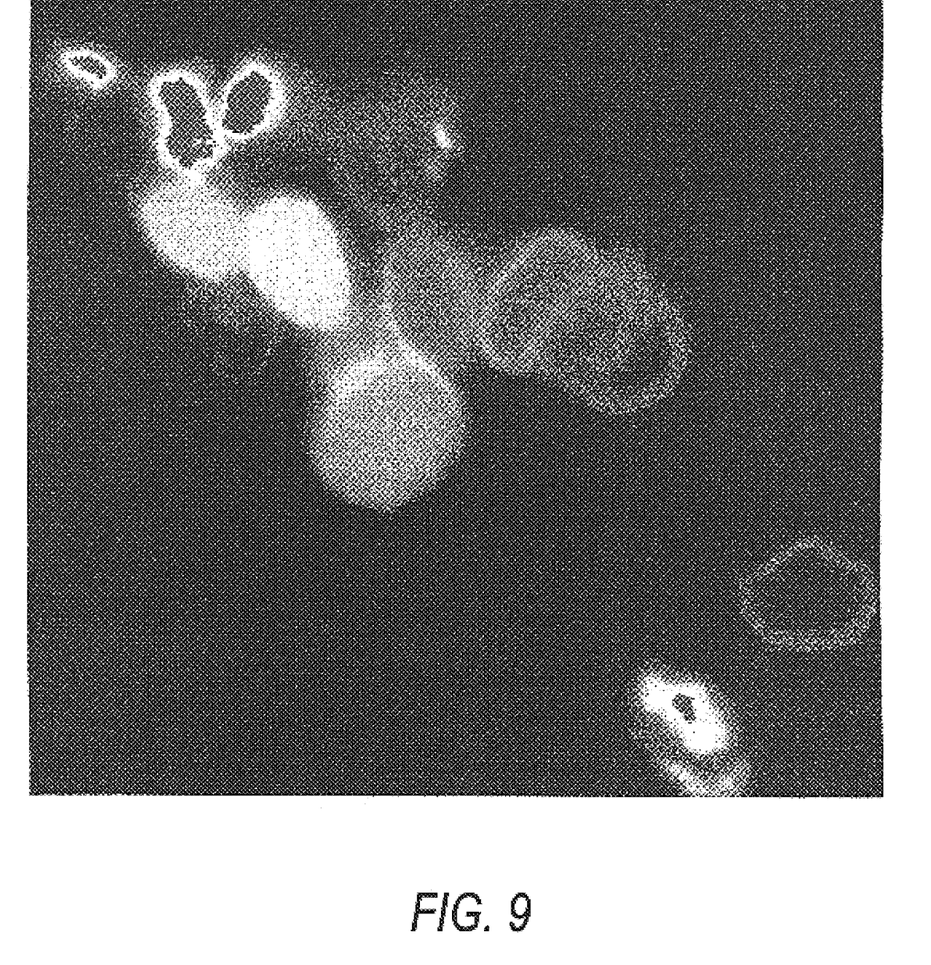
FIG. 9 the formation of poly(diallyldimethylammonium chloride) by free-radical polymerization on the outside and in the inside of polyelectrolyte shells.

FIG. 9 shows the result of a free-radical polymerization of diallyldimethylammonium chloride (DADMAC) in PAH/PSS shells. For this purpose, a 3% strength monomer solution in a 2% strength suspension of capsules was mixed with the polymerization initiator sodium peroxodisulfate (30 mg/100 ml) and polymerized at 70° C. for 9.5 h. The polymer PDADMAC synthesized in the volume phase was removed by centrifugation. After treatment with 100 mM 6-CF, the binding of the dye to the amino groups of PDADMAC is clearly evident. The polymer is adsorbed onto the negative capsule walls, but is also to be found inside the capsules.

Polyelectrolyte shells consisting of nine layers ([PSS/PAH]$_4$PSS) were deposited on human erythrocytes, and the template particles were removed. A further FAH layer was then applied. The capsules were used for free-radical polymerization of acrylic acid to polyacrylic acid. For this purpose, a 3% strength monomer solution in a 2% strength suspension of capsules was mixed with the initiator sodium peroxodisulfate (30 mg/100 ml) and polymerized at 70° C. for 9.5 h. The polyacrylic acid synthesized in the volume phase was removed by centrifugation. After addition of 100 nM rhodamine B (which binds selectively to anionic groups) it was possible to detect the presence of polyacrylic acid adsorbed onto the negatively charged capsule walls, but also inside the capsules. Flocculation of the capsules took place because of a bridge formation mediated by acrylic acid. This adsorption of the acrylic acid can be prevented by using capsules with an external negative charge.

What is claimed is:

1. A process for producing capsules with a polyelectrolyte shell, which comprises applying several consecutive layers of oppositely charged polyelectrolyte molecules to a template selected from aggregates of biological or/and amphiphilic materials by initially producing a dispersion of the template particles in an aqueous solution, then adding a polyelectrolyte species with the same or the opposite charge as the surface of the template particle to this dispersion, subsequently, after removing any excess polyelectrolyte molecules present, adding the oppositely charged polyelectrolyte species used to build up the second layer, and then where appropriate applying further alternately oppositely charged layers of polyelectrolyte molecules, and subsequently disintegrating the template where appropriate.

2. The process as claimed in claim 1, wherein identical or different polyelectrolyte species or mixtures of polyelectrolyte species are selected for each layer with the same charge.

3. The process as claimed in claim 1, wherein two to forty polyelectrolyte layers are applied.

4. The process as claimed in claim 3, wherein four to twenty polyelectrolyte layers are applied.

5. The process as claimed in claim 1, wherein a template selected from the group consisting of cells, cell aggregates, subcellular particles, virus particles and aggregates of biomolecules is used.

6. The process as claimed in claim 1, wherein pollen is used as template.

7. The process as claimed in claim 1, wherein a template selected from the group consisting of vesicles, micelles and lipid aggregates is used.

8. The process as claimed in claim 1, wherein the template is pretreated with a fixing reagent.

9. The process as claimed in claim 1, wherein formaldehyde or/and glutaraldehyde is used as fixing reagent.

10. The process as claimed in claim 1, wherein a partially disintegrated template is used as starting material for the application of the polyelectrolyte molecules.

11. The process as claimed in claim 10, wherein the template has a toroidal structure.

12. The process as claimed in claim 1, wherein the template is disintegrated by adding a lytic reagent.

13. The process as claimed in claim 12, wherein the lytic reagent contains a deproteinizing agent selected from peroxo and hypochlorite compounds.

14. The process as claimed in claim 13, wherein sodium or potassium hypochlorite is used as deproteinizing agent.

15. The process as claimed in claim 1, wherein at least one lipid layer is deposited on the polyelectrolyte shell after disintegration of the template.

16. The process as claimed in claim 15, wherein at least one further polyelectrolyte layer is deposited on the lipid layer.

17. The process as claimed in claim 1, wherein an active ingredient is introduced into the capsules.

18. The process as claimed in claim 1, wherein the active ingredient is selected from catalysts, active pharmaceutical ingredients, polymers, dyes, sensor molecules, aroma substances and crop protection agents.

19. The process as claimed in claim 1, wherein organic liquids or gases are introduced into the capsules.

20. The process as claimed in claim 1, wherein a chemical reaction, is carried out in or/and on the capsules.

21. The process as claimed in claim 1, wherein a precipitation or crystallization is carried out in or/and on the capsules.

22. A polyelectrolyte capsule obtainable by a process as claimed in claim 1, which comprises a template particle in its interior.

23. A polyelectrolyte capsule obtainable by a process as claimed in claim 1, which has a diameter in the range from 10 nm to 10 $\mu$m.

24. A polyelectrolyte capsule obtainable by a process as claimed in claim 1, which has a wall thickness of the polyelectrolyte layers in the range from 2 to 100 nm.

25. A capsule as claimed in claim 23, which comprises the template particle in its interior.

26. A capsule as claimed in claim 23, which comprises no detectable template residues.

27. A capsule as claimed in claim 1, has an external shape predetermined by the template particle.

28. A capsule as claimed in claim 27, which has an anisotropic shape.

29. A capsule as claimed in claim 28, which has a toroidal shape.

30. A capsule as claimed in claim 22, which comprises an active ingredient.

31. An anisotropic particle composition obtainable by encapsulating active ingredients in capsules as claimed in claim 28 and removing the polyelectrolyte shell.

32. A composition as claimed in claim 31 in the form of a dispersion.

33. A method of encapsulating an emulsion comprising encapsulating an emulsion inside the capsule of claim 22.

34. A method of performing a chemical reaction comprising conducting a chemical reaction in the polyelectrolyte capsule of claim 22.

35. A method of precipitating a substance comprising precipitating a substance from a solution in the polyelectrolyte capsule of claim 22.

36. A method of crystallizing a substance comprising crystallizing a substance in the capsule of claim 22, wherein said capsule is a template for the shape of the resultant crystal.

37. A method of preparing a capsule, comprising encapsulating an active ingredient in the capsule of claim 22.

38. A sensor system comprising a sensor and the capsule of claim 22.

39. A surface analysis system comprising the capsule of claim 22.

40. A pharmaceutical comprising a pharmaceutical agent encapsulated in the capsule of claim 22.

41. A cosmetic comprising the capsule of claim 22 and at least one cosmetically suitable compound.

42. An edible food product comprising the capsule of claim 22.

43. A printing product comprising printing dye encapsulated in the capsule of claim 22.

44. A microcomposite comprising the capsule of claim 22.

45. A nanocomposite comprising the capsule of claim 22.

46. The process as claimed in claim 20, wherein the chemical reaction is a polymer synthesis.

* * * * *